US005830725A

United States Patent [19]

Nolan et al.

[11] Patent Number: 5,830,725
[45] Date of Patent: Nov. 3, 1998

[54] RAPID, STABLE HIGH-TITRE PRODUCTION OF RECOMBING RETROVIRUS

[75] Inventors: Garry P. Nolan, Palo Alto; Todd Kinsella, Mountain View, both of Calif.

[73] Assignee: The Board of Trustees for the Leland Stanford Junior University, Palo Alto, Calif.

[21] Appl. No.: 430,813

[22] Filed: Apr. 28, 1995

[51] Int. Cl.[6] .............................. C12N 15/00; C12N 5/00; A61K 48/00; C07K 14/00

[52] U.S. Cl. .............................. 435/172.3; 435/320.1; 435/240.2; 514/44; 530/350

[58] Field of Search .............................. 424/93.21, 93.2; 435/320.1, 240.2, 172.3, 240.1; 514/44

[56] References Cited

U.S. PATENT DOCUMENTS

| | | | |
|---|---|---|---|
| 4,686,186 | 8/1987 | Sugden | 435/243 |
| 4,939,088 | 7/1990 | Young et al. | 435/69.51 |
| 5,173,414 | 12/1992 | Lebkowski et al. | 435/172.3 |
| 5,194,601 | 3/1993 | Sugden et al. | 435/320.1 |
| 5,278,056 | 1/1994 | Bank et al. | 435/172.3 |
| 5,324,645 | 6/1994 | Takahara et al. | 435/172.1 |
| 5,449,614 | 9/1995 | Danos et al. | 435/172.3 |

FOREIGN PATENT DOCUMENTS

| | | |
|---|---|---|
| 488528 | 6/1992 | European Pat. Off. . |
| 9419478 | 9/1994 | WIPO . |

OTHER PUBLICATIONS

Pear et al., Proc. Natl. Acad. Sci. USA, 90:8392–8396 (1993).

Heinzel et al., J. of Virology, 62(10):3738–3746 (1988).

Yee et al., Methods in Cell Biology, 43:99–112 (1994).

Miller et al., Biotechniques, 7(9):980–990 (1989).

Sarasin, A., J. Photochemistry and Photobiology, 3:143–155 (1989).

Yates et al., Proc. Natl. Acad. Sci. USA, 81:3806–3810 (1984).

Yates et al., Nature, 313:812–815 (1985).

Morgenstern et al., Nucleic Acids Research, 18(12):3587–3596 (1990).

Soneoka et al., Nucleic Acids Research, 23(4):628–633 (1995).

Markowitz et al., Virology, 167:400–406 (1988).

Cone et al., Proc. Natl. Acad. Sci. USA, 81:6349–6353 (1984).

Danos et al., Proc. Natl. Acad. Sci. USA, 85:6460–6464 (1988).

*Primary Examiner*—Suzanne E. Ziska
*Assistant Examiner*—Andrew Milne
*Attorney, Agent, or Firm*—Richard Aron Osman

[57] ABSTRACT

High titre helper-free recombinant retrovirus are produced by (a) growing a transfected host cell, produced by transfecting a eukaryotic host cell with a recombinant vector capable of stable episomal maintenance in the host cell, in a medium under conditions whereby the recombinant vector is stably maintained as an episome in the transfected host cell and transcripts of said vector form, with retroviral gag, pol and env gene products, an infectious retrovirus; and (b) isolating from the medium helper-free infectious retrovirus formed in the transfected host cell. The recombinant vectors comprise (i) a retroviral construct comprising an exogenous gene; (ii) a eukaryotic origin of replication sequence providing a substrate for replicase activity capable of replicating the vector in the host cell; and, (iii) a copy control sequence providing a substrate for a copy control activity capable of maintaining the vector at a stable copy number in the host cell. The transfected host cell provides retroviral pol reverse transcriptase and integrase activity, the replicase activity and copy control activity, as well as retroviral gag and env gene products capable of forming, with a transcript of the retroviral construct, an infectious retrovirus.

23 Claims, 4 Drawing Sheets

RAPID, STABLE HIGH-TITRE PRODUCTION OF RECOMBING RETROVIRUS

INTRODUCTION

Technical Field

The technical field of this invention is the stable, high-titre production of recombinant retroviruses.

Background

Currently, the most successful gene transfer methodologies harness the capacity of engineered viruses, such as retroviruses, to bypass natural cellular barriers to exogenous nucleic acid uptake. The classic approach to the generation of recombinant retroviruses was pioneered by Richard Mulligan and David Baltimore in the creation of the Psi-2 and analogous retrovirus packaging systems, based on NIH 3T3 cells. These helper-defective packaging lines are capable of producing all the necessary trans proteins -gag, pol, and env- that are required for packaging, processing, reverse transcription, and integration of recombinant genome. Those RNA molecules that have in cis the Ψ packaging signal are packaged into maturing virions. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

Despite their several advantages, recombinant retrovirus use in research industries and clinical settings has been critically hampered by key technical hurdles. To be useful in gene therapy, and other settings, the titre of the producer line must be about $10^5$ virions per ml, or greater. For each recombinant construct it is necessary to test many clonal cell lines to find the one that stably produces high titre recombinant virus. This can take an average of two months, is labor-intensive, and limits the constructs one can convert to retrovirus in a reasonable time period. The demand for more efficient reagents and methods for producing recombinant retrovirus for gene therapy is urgent. Pending applications include correcting genetic defects, engineer stem cells in leukemia therapies and T-cell populations in HIV-1 infection.

An initial attempt to overcome such limitations was a transient retrovirus production technique, the BOSC23 producer system, for the rapid production of high titre helper-fee recombinant retrovirus. BOSC23 is a cell line and system capable of generating within three days up to $10^7$ per ml helper-free recombinant retrovirus/ml (See, Pear, W. S., Nolan, G. P., Scott, M. L., and D. Baltimore. 1993 Production of high-titer helper free retrovirus by transient transfection. Proc. Natl. Acad. Sci. USA 90(18):8392–6). The system relies on a human cell line, 293, that can be induced to efficiently take up and express extremely high levels of transiently-introduced DNA. A 293 cell subclone was stably transfected with gag-pol, and env, thus endowing the line with the ability to make all the necessary proteins to package retroviral genomic RNA. When defective retroviral constructs are transfected into this line, high titre retrovirus are produced within three days.

The transient system was conceived out of a need to rapidly produce viruses from the numerous retroviral constructs often used in standard gene transfer experimentation. However, even though the ecotropic BOSC23 system as described has great utility, its use in gene therapy and related applications is limited due to its tropism to murine and rat cells. This limitation was addressed more recently with an amphotropic equivalent of BOSC: a 293-based system for the production of amphotropic virus capable of infecting human cells. Briefly, a cell line was created by co-transfection of 293 cells with amphotropic envelope protein and the selectable marker gpt. After selection, pools of clones expressing amphotropic envelope were stained with primary antibody to amphotropic envelope (83A25) followed by a second step phycoerythrin conjugated antibody to 83A25. Cells expressing envelope protein were cloned by FACS. Clones were later tested for both their level of expression of amphotropic envelope and uniformity of expression. Out of approximately 50 clones tested, one clone (#18) was found to express high, uniform levels of amphotropic envelope protein. Clone #18 was then stably transfected with gag-pol. A clone expressing gag-pol and amphotropic envelope, termed BING, was derived that produces high-titre, helper-free recombinant retrovirus after transient transfection of a suitable retrovirus construct.

For maximal commercial utilization in both clinical practice and the biopharmaceutical research industries, large volumes of retrovirus material are necessary. Unfortunately, technical limitations to transfection into 293 cells limits their utility in transient production of virus in large volumes. Currently, methodology conveniently allows for production of up to 50 ml of retroviral supernatant. While the NIH 3T3-based helper-producer systems allow for large volume production, the transfection efficiency is low and hence time and labor requirements are high. Because of these limitations, we sought to develop a novel transduction system capable of efficiently providing rapid stable, high-titre production of retroviruses with ecotropic, amphotropic and polytropic host ranges.

Relevant Literature

Mann et al. (1983) Cell 33, 153–159, Pear et al. (1993) Proc. Natl. Acad. Sci. USA 90(18):8392–6 and copending U.S. patent application Ser. No. 08/023,909 describe the BOSC and BING systems. Epstein-Barr virus-based vectors (which do not produce retrovirus, require helper virus function and operate on entirely different replicative and transcriptive mechanisms than the subject vectors) are described in Lebkowski et al. (1992) U.S. Pat. No. 5,173,414.

SUMMARY OF THE INVENTION

Methods and compositions for making and using high titre helper-free recombinant retrovirus are provided. In general, the methods involve (a) growing a transfected host cell, produced by transfecting a eukaryotic host cell with a recombinant vector capable of stable episomal maintenance in the host cell, in a medium under conditions whereby the recombinant vector is stably maintained as an episome in the transfected host cell and transcripts of said vector form, with retroviral gag, pol and env gene products, an infectious retrovirus; and (b) isolating from the medium helper-free infectious retrovirus formed in the transfected host cell. Resultant retrovirus are useful in a wide variety of gene therapy applications.

The recombinant vectors used in the method generally comprise (i) a retroviral construct comprising, usually in 5' to 3' orientation, a first regulatory region providing cis-necessary 5' sequences for retroviral reverse transcription and integration, a retroviral packaging signal, an exogenous gene operably linked to a transcription regulatory element, and a second regulatory region providing cis-necessary 3' sequences for retroviral reverse transcription and integration activity; (ii) a eukaryotic origin of replication sequence providing a substrate for replicase activity capable of replicating the vector in the host cell; and, (iii) a copy control sequence providing a substrate for a copy control activity capable of maintaining the vector at a stable copy number in the host cell. The transfected host cell provides retroviral pol reverse transcriptase and integrase activity, the replicase activity and copy control activity, as well as retroviral gag and env gene products capable of forming, with a transcript of the retroviral construct, an infectious retrovirus.

In preferred embodiments the recombinant vector further comprises variously a eukaryotic selectable marker operably linked to a transcription regulatory element, a prokaryotic selectable marker operably linked to a transcription regulatory element, and a prokaryotic origin of replication sequence providing a substrate for replicase activity capable of replicating the vector in a prokaryotic cell; the copy control sequence is a nuclear retention sequence providing a substrate for a nuclear retentase activity capable of retaining the vector in the nucleus of the host eukaryotic cell; the medium comprises a selective agent permitting the selective growth of eukaryotic cells expressing the eukaryotic selectable marker; both the origin of replication and the nuclear retention sequence of the recombinant vector are provided by a single continuous viral ori sequence; the host cell is stably transfected with nucleic acid encoding the gag and pol genes which are both operably linked to a transcription regulatory element, and a viral gene, the transcription product of which provides both the replicase and nuclear retentase activity; and the isolating step comprises isolating at least $10^7$ helper-free infectious retrovirus per milliliter medium.

DETAILED DESCRIPTION OF THE INVENTION

Figure 1:
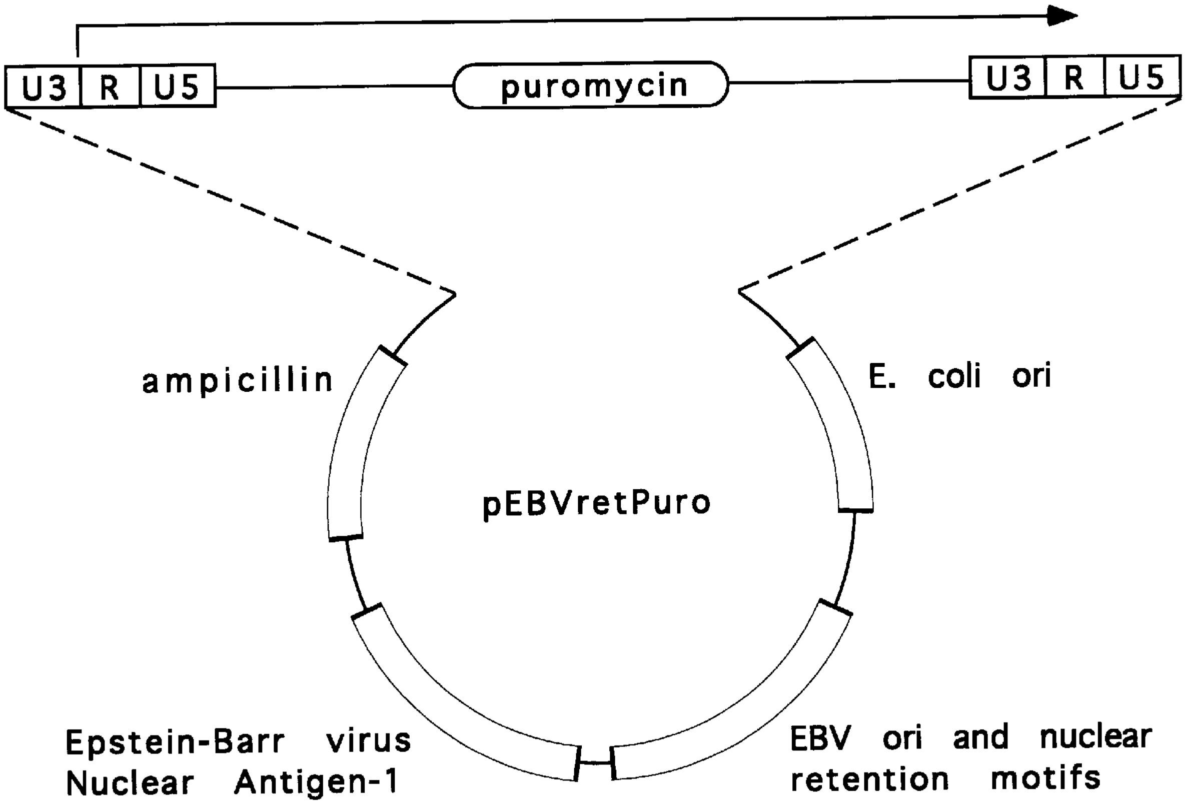
FIG. 1. Design of pBabePuro$^{220}$/pEBVretPuro retrovirus vector.

The invention provides methods and compositions for efficiently making high titre helper-free recombinant retrovirus in a variety of host cells. The methods are rapid: establishment of the vectors in up to 100% of the host cell population can occur within only a few days. The methods can generate large numbers of producer cells for sustained periods of time, permitting the collection of large volumes of retrovirus. With such large production volumes, titres may be increased still further by concentration. The methods may be practiced in a wide variety of cell types including conventional lines such as HeLa cells. The methods find a wide variety of industrial and academic applications in biomedical research, development and production/manufacturing programs, therapeutic applications such as in gene therapy (e.g. inhibit HIV-1 expression), infection of somatic cells to effect gene replacement therapy, etc.

The present invention takes the best qualities of the transient system for generating recombinant retrovirus, which is limited to the ready production of up to 50 ml of high titre supernatant per virus and weds it to the advantages of long-term outgrowth of retroviral producer lines. Thus, the present systems are capable of rapidly producing several liters (if necessary) of high titre viral supernatant within a few weeks of construction of a given recombinant retrovirus. In addition, among the several advantages inherent, this approach makes more efficient the production of suitable quantities of high-titre retrovirus for the biomedical and pharmaceutical research industries and clinical practice, particularly gene and cell therapies.

The subject methods involve growing a eukaryotic host cell transfected with a recombinant vector capable of stable episomal maintenance in the host cell. The vectors comprise a retroviral construct comprising an exogenous gene, a eukaryotic origin of replication sequence providing a substrate for replicase activity capable of replicating the vector in the host cell and a copy control sequence providing a substrate for a copy control activity capable of maintaining the vector at a stable copy number in the host cell. The retroviral constructs comprise the exogenous gene of interest and/or an exogenous gene insertion site flanked upstream and downstream by retrovirus regulatory sequences necessary for retroviral production from the transfected host cell. The virus may also comprise retrovirus coding sequences, though to maximize vector space available to the exogenous gene and to ensure production of helper-defective recombinant retrovirus, the host cell frequently encodes both pol and gag retroviral translation products and often all necessarily retroviral translation products including env. Typically, genes encoding these products are stably engineered into the host cell prior to transfection with the subject vectors. The env gene may be retained in the construct to provide a particular vector-tropism or host cell specificity, see e.g. Kasahara, N., Dozy, A. M., and Y. W. Kan. (1994) Science 266(5189):1373–6. The up- and downstream regulatory regions flanking the exogenous gene include a 5' retroviral packaging signal and additional 5' and 3' retroviral cis-necessary sequences for retroviral reverse transcription and proviral integration such that the construct is capable of generating proviral DNA when the retrovirus infects a target cell. The cis necessary sequences include a primer binding site (PBS) and 5' and 3' integrase binding sites, see Reverse Transcriptase, Ed. Stephen Goff, Cold Spring Laboratory Harbor Press. The constructs may employ natural retroviral sequences providing the requisite reverse transcriptase substrate activity or mutated natural cis-necessary sequences or synthetic sequences so long as they provide a functional substrate for the reverse transcriptase and integrase activities. Exemplary natural packaging signals and 5' and 3' cis necessary sequences for retroviral reverse transcriptase and integration activities include the sequences shown in Table 1.

TABLE 1

| |
|---|
| Packaging Signals ($\psi$): |
| Moloney Murine Leukemia Virus (Mo-MuLV) Weiss et al. (1985) RNA Tumor Viruses, 2nd Ed., Cold Spring Harbor Laboratory pg. 770 |

TABLE 1-continued

UGG CCA GCA ACU UAU CUG UGU CUG UCC GAU UGU CUA GUG UCU
AUG ACU GAU UUU AUG CGC CUG CGU CGG UAC UAG UUA GCU AAC
UAG CUC UGU AUC UGG CGG ACC CGU GGU GGA ACU GAC GAG UUC
GGA ACA CCC GGC CGC AAC CCU GGG AGA CGU CCC AGG GAC UUC
GGG GGC CGU UUU UGU GGC CCG ACC UGA GUC CAA AAA UCC CGA
UCG UUU UGG ACU CUU UGG UGC ACC CCC CUU AGA GGA GGG AUA
UGU GGU UCU GGU AGG AGA CGA GAA CCU AAA ACA GUU CCC GCC
UCC GUC UGA AUU UUU GCU UUC GGU UUG GGA CCG AAG CCG CGC
CGC GCG UCU UGU CUG (SEQ ID NO: 1)

Rous Sarcoma Virus (RSV), See e.g. Aronof and Linial (1991) J. Virol. 65(1):71–80

EcoR1-Xho-1 fragment of RSVclone pATV8R (Katz et al. (1982) J. Virol. 42(1): 346–351)

Human Immunodeficiency Virus, Type 1 (HIV-1), See e.g. Hayashi et al Virol 188:590–599

CGC CAA AAA TTT TGA CTA GCG GAG GCT AGA AGG AGA GAG ATG
GGT G (SEQ ID NO: 2)

Primer Binding Sites:

HIV-1 (5' UGG CGC CCG AAC AGG GAC 3') (SEQ ID NO: 3)
See e.g., Wakefield et al. (1994) J. Virol. 68(3):1605–1614
Mo-MuLV (5' UGG GGG CUC GUC CGG GAU 3') (SEQ ID NO: 4)
See e.g., Weis et al (1985) RNA Tumor Viruses 2nd, Cold Spring Harbor Laboratory, pp. 770.
RSV (5' UGG UGA CCC CGA CGU GAU 3') (SEQ ID NO: 5)
See e.g., Weis et al (1985) RNA Tumor Viruses 2nd, Cold Spring Harbor Laboratory, pp. 770.

Integrase Binding Sites:

HIV-1, See e.g. Hazud et al. (1994) J. Biol. Chem. 269(6):3999–4004
U3 LTR 5' AG TGA ATT AGC CCT TCC A GT (SEQ ID NO: 6)
U5 LTR 5' TGT GGA AAA TCT CTA GCA GT (SEQ ID NO: 7)
Mo-MuLV, See e.g. Murphy et al. (1993) Virology 195:432–440
U3 LTR 5' AAT GAA AGA CC (SEQ ID NO: 8)
U5 LTR 5' GGG TCT TTC ATT (SEQ ID NO: 9)

A wide variety of endogenous (not naturally part of the retrovirus) genes may be used, depending on the intended application of the retrovirus. The term gene as used herein broadly encompasses sequences providing a wide variety of transcripts, as describe below, in addition to transcripts encoding proteins. Generally, the constructs limit the insert size to under about 10 kb. To construct the recombinant vector, the exogenous gene of interest is inserted into a blank vector at a convenient cloning/insertion site (e.g. a predetermined restriction site or polylinker). The gene is operably linked to a transcription regulatory element for expression in the target cell, which expression may be constitutive or induced. Depending on the application, transcripts of the gene may provide RNA endproducts (e.g. therapeutic antisense RNA, ribozyme components, etc.), message encoding active proteins (e.g. regulators of cell growth, mediators of signal transduction, etc.), message encoding active peptides (e.g. inhibitors of transcription, viral infection or signal transduction, etc.), etc.

In addition to the retroviral construct, the vectors comprise eukaryotic origin of replication (ori) and copy control sequences. These sequences are necessary for episomal replication and copy number control in the host cell. The copy number control sequence provides an approximately constant episomal copy number through repeated cell cycling; typically by effecting a single episomal replication per cell cycle. The ori and copy control sequences may overlap fully or partially or be separated. The ori sequence provides a substrate for replicase activity capable of replicating the vector in the host cell and the copy control sequence provides a substrate for a copy number control activity. A variety of copy control sequences and activities may be used to maintain episomal copy number though cell divisions. Preferred sequences derive from double-stranded DNA Herpes-type viruses, e.g. Epstein-Barr virus (EBV), human papilloma virus (HPV), bovine papilloma virus (BPV), etc. In a preferred embodiment, the copy control sequence is a nuclear retention sequence providing a substrate for a nuclear retentase activity capable of retaining said vector in the nucleus of said host cell. The nuclear retention sequence provides a substrate for a nuclear retentase activity capable of retaining the vector in the nucleus of the host cell. These episomal replicative and copy control activities may be encoded by the episomal vector or by genetic material stably introduced into the host cell prior to transfection and may be provided by one or a plurality of proteins. Table 1 provides a number of exemplary sequence substrates—protein combinations which may be used in the subject constructs to effect stable episomal maintenance of the vector.

TABLE 2

Substrate-protein combinations conferring stable episomal maintenance.

| | Substrate Sequences | Protein Activities |
|---|---|---|
| 1. | EBV Orip (family of repeats and dyad) | EBNA-1 |
| 2. | EBV family of repeats and host functions | EBNA-1 and host replication |
| | replication sequences | |
| 3. | BPV Ori | BPV E1 and E2 proteins |
| 4. | HPV Ori | HPV E1 and E2 proteins |
| 5. | DPV Ori | DPV E1 and E2 proteins |
| 6. | EEPV Ori | EEPV E1 and E2 proteins |
| 7. | CRPV Ori | CRPV E1 and E2 proteins |

Of the various latent replication functions listed in Table 2, most are known to maintain vectors episomally at copy numbers of under 1,000 per cell. Increasing the number of vector copies, even if only transiently, can potentially lead to increases in the total yield of infectious virus (titer). A number of viral lytic replication functions can be exploited to provide amplification of vector copy number over that typically maintained by latent replication functions such as Orip/EBNA-1 of EBV. For example, plasmids that contain the SV40 origin of replication are capable of replicating to extremely high copy numbers (10,000–100,000 copies/cell) in the presence of SV40 large T-antigen (Tsui, L. C., Breitman M. L., Siminovitch, L., and M. Buchwald. 1982. Persistence of freely replicating SV40 recombinant molecules carrying a selectable marker in permissive simian cells, Cell 30: 499–508). Chimeric vectors containing latent replication functions of the Epstein-Barr virus (Orip/EBNA-1) as well as SV40 origin sequences, replicate predominantly in a lytic mode in the presence of functional SV40 large T-antigen.

In a particular embodiment, the subject vectors also contain lytic replication functions which allow amplification of vector copy number above that typically maintained by latent replication/retention functions as listed in Table 2. Table 3 provides several exemplary sequence-protein combinations which may be used in the subject constructs to affect transient increases in vector copy number.

TABLE 3

Viral cis and trans replication functions conferring stable episomal maintenance and transient amplification of episomal copy number.

| | Substrate Sequence | Protein Activity | |
|---|---|---|---|
| 1. | EBV Orip | EBNA-1 | Low copy rep. and retention function |
| | SV40 Ori | SV40 Large T-Antigen | Amplification function |
| 2. | EBV Orip | EBNA-1 | Low copy rep. and retention function |
| | Polyoma Ori | Polyoma Large T-Antigen | Amplification function |
| 3. | EPV Orip | EBNA-1 | Low copy rep. and retention function |
| | EBV Ori Lyt | ZEBRA | Amplification function |

Proteins necessary for the lytic replication of these vectors may be provided by a number of different strategies such as co-transfection of appropriate expression constructs, placement of the necessary genes within the subject vector and the creation of cell lines which stably express any necessary lytic replication proteins. Additionally, temperature sensitive mutants of lytic replication proteins or the regulated expression of genes for these lytic functions (tet inducible promoter system) may be utilized for more precise control of lytic replication.

Frequently the subject vectors also comprise a eukaryotic selectable marker operably linked to a transcription regulatory element to select for transfected host cells. For cloning, manipulation and production of the vector in a prokaryotic host, the vector also frequently comprises a prokaryotic selectable marker operably linked to a transcription regulatory element and a prokaryotic origin of replication sequence providing a substrate for replicase activity capable of replicating the vector in the prokaryotic cell.

A wide variety of host cells may be used depending on the nature of the target cell and the vector. Preferred host cells are highly transfectable, have vigorous growth characteristics in a wide variety of media, and can be adapted to large scale culture such as spinner culture, thus allowing for very high density cell growth and retroviral production. For most applications of the subject methods, it is critical that the host cell line does not contain endogenous retrovirus genomes which could contaminate the desired recombinant retrovirus. Exemplary suitable cell lines include human 293 cells, HeLa cells, human B cells, MOLT4 T cells, U937 macrophage cells, etc. For some target cell applications, co-cultivation can increase infection effeciency by cell—cell contact, e.g. use adherent producer cells to allow co-cultivation with target suspension cells. For example, for stem cell targets a strongly adherent fibroblastic producer such as HeLa cells provides excellent producers where the stem cell is co-cultivated during infection and later removed. Alternatively, a suspension of cells such as MOLT4 or Jurkat may be used as retroviral producers for co-cultivation with a fibroblastic or adherant target cell.

As describe above, the gene product(s) necessary for episomal maintenance function need not be encoded on the episome. Frequently, the host cells are stably transfected before and/or after transfection with the subject vectors with nucleic acids encoding gene products necessary for episomal maintenance and retroviral production. Examples of such cells lines include the 293-based BOSC23 and BING retroviral producer cells. For instance, transfection of 30 ug of retroviral plasmid with episomal maintenance function into $10^7$ BOSC23 or BING cells yields a transfected population of $2.5\times10^6$ producer cells. After 6 days selection for the episome, providing a cell doubling time of 16 hours, a population of $1.28\times10^9$ episome-containing cells is obtained.

Transfection of the eukaryotic host cell with the subject vectors may be performed by any convenient method. Exemplary methods include $CaPO_4$ precipitation, liposome fusion, lipofectin®, electroporation, etc. For example, the subject vectors can be complexed with the cationic lipid DOTMA (N-[1-(2,3-dioleyloxy)proply]-N,N,N-triethylammonium) and the neutral lipid DOPE (dioleoyl phosphatidylethanolamine) to form unilamellar liposomes. Typical ratios are 1–10 ug of DNA and 100 ug total lipid (DOTA/DOPE 1:1 by weight) in a total volume of 3 ml of Hepes-buffered saline solution. Nearly confluent cell culture (100 mm tissue culture plate) are overlayed with the above mentioned lipid-DNA mixture and incubated at 37° C. for 5 hours. Ten ml of serum supplemented with Dulbecco's Modified Eagle's Medium is added after the initial incubation period and cells are then incubated at 37° C. for an additional 16 hours. At 24 hours post-lipofection, the medium is replaced with 10 of fresh medium. HeLa cells are transfected to >50% expression after two days using this transfection method.

Transfected cells comprising the requisite components for retroviral production and episomal maintenance are grown in a medium under conditions whereby the recombinant vector is stably maintained as an episome in the transfected host cell and transcripts of said vector form, with retroviral gag, pol and env gene products, infectious retrovirus. Frequently, the medium comprises a selective agent to permit the selective growth of eukaryotic cells expressing a eukaryotic selectable marker. Exemplary selective agent—selectable marker combinations include puromycin—puromycin resistance gene (pac); blastomycin—blastomycin resistance gene; antibody/FACS—surface marker. See, e.g. Krasnow, M. A., Cumberledge S., Manning, G., Herzenberg, L. A., and G. P. Nolan. 1991 Whole animal cell sorting of Drosophila embryos. Science. 251(4989):81–5; and Fiering, S. N., Roederer, M., Nolan, G. P., Micklem, D. R., Parks, D. R., and L. A. Herzenberg. Improved FACS-Gal: flow cytometric analysis and sorting of viable eukaryotic cells expressing reporter gene constructs. Cytometry 12(4):291–301. Additional growth and selective media and suitable selective markers and selectable markers are well known in the art.

The transfected cells are capable of stable production of retrovirus. Generally stable producer cells provide high-titre retrovirus over at least two weeks, preferably at least 8 weeks and more preferably at least 32 weeks. Resultant high-titre helper-free infectious retrovirus formed in the transfected host cells are then isolated from the media. Generally, viral titer of the medium exceeds $3\times10^6$ helper-free infectious retrovirus per milliliter medium and preferred systems provide titres exceeding $10^7$, preferably exceeding $3\times10^7$, more preferably exceeding $10^8$, more preferably exceeding $3\times10^8$, most preferably exceeding $10^9$.

The following experimental section/examples are offered by way of illustration and not by way of limitation.

EXPERIMENTAL

MATERIALS AND METHODS

Plasmids.

pBabePuro contains LTR and Ψ packaging sequences from the Muloney Murine Leukemia Virus (Mo-MuLV). The puromycin resistance gene is present within the retroviral backbone and under the control of the SV40 early promoter.

pBabePuro(DSV40) is a derivative of pBabe Puro in which the SV40 early promoter has been removed by digestion with SalI and HindIII, followed by an end filling reaction with klenow and religation of the blunted vector.

pBabePuro(DSV40)A was constructed by the insertion of an adapter (5'-BglII-HindIII-XhoI-EcoRI-3') into a unique NotI site present within the backbone of pBabePuro (DSV40) A; The NotI site was not reconstructed.

p220.2 contains the EBV EBNA-1 gene, EBV Orip cis elements and the hygromycin resistance gene in a standard pBR322 backbone (TJ14). EBNA-1 is expressed under the control of a cryptic promoter auspiciously present in pBR322 sequences (TJ). Proximal to the Orip sequences are termination sequences from the herpes simplex virus type-1 thymidine kinase gene. (TJ14).

PGKPuro was created by ligating the puromycin resistance gene and SV40 polyadenylation sequences (PstI-BamHI fragment) from the plasmid pPUR into the PstI and BamHI sites of the plasmid PGKNeo-SUT-1. The resulting vector contained the SV40 polyadenylation sequences and the puromycin resistence gene driven by the phosphoglycerol kinase-1 promoter (PGK-1).

pBabePuro-LacZ is a derivative of pBabePuro in which the LacZ gene, obtained from the plasmid AVRZ ( DraI-DraI fragment), has been blunted into the SnaBI polylinker site of pBabe Puro.

pBabeM is a retroviral vector constructed using the 5' LTR and Ψ packaging sequences of the MFG vector (Pst I-BamHI fragment) and the LacZ gene and 3' LTR of pBabePuro-LacZ. Polylinker sequences that flank the LacZ gene of pBabeM were constructed using a DNA synthesizer and standard techniques.

$pBabePuro^{220}$ was created using sequences from pBabe Puro(A) and p220.2. Briefly, pBabePuro was digested with Sal I and Hind III, blunted and religated to create pBabePuro (DSV40). A small adapter (5' Bgl II,Hind III, Xho I, EcoRI-3') was then inserted into the unique Not I site of pBabePuro (DSV40). The EcoRI-1 BamHI fragment of p220.2, which contains the EBV Orip elements and the EBNA-1 gene, was inserted into the Bgl II and EcoRI adapter sites of pBabePuro(DSV40)A to create $pBabePuro^{220}$.

LZRS-LacZ was created using sequences derived from $pBabePuro^{220}$ and pbabe M. The construction of LZRS-LacZ was as follows: an adapter containing EcoRI and Bgl II sites was inserted into the EcoRI site of $pBabePuro^{220}$. The EcoRI-BamHI fragment of PGKPuro, which contained the PGK-1 promoter, the puromycin resistance gene and SV40 polyadenylation sequences, was then placed into the EcoRI and BamHI sites of the adapter. The transcriptional orientation of the PGKPuro EcoRI-BamHI fragment is opposite that of the EBNA-1 gene.

$pSV40LacZ^{220}$ was derived from retroviral portions of pBabePuroLacZ and the Epstein-Barr virus sequences present within LZRS-LacZ: BspHI digestion of both LZRS-LacZ and pBabePuroLacZ, followed by ligation of the appropriate fragments, yielded $pSV40LacZ^{220}$.

Cell lines and tissue culture.

BOSC 23 cells are an ecotropic retroviral packaging cell line constructed from human 293T cells as previously described. The BING retroviral packaging cell line is the amphotropic equivalent of the BOSC 23 system and was constructed as describe supra. Both the BOSC 23 ecotropic and the BING amphotropic lines were grown in Dulbecco's modified Eagle medium that had been supplemented with 10% fetal calf serum (Applied Scientific), 1% glutamine and 1% pen-strep. NIH 3T3 cells were maintained in Dulbecco's modified Eagle medium, 10% calf serum, 1% glutamine and 1% pen-strep. All cell lines were grown at 37° C. and 5% $CO_2$.

Transfections.

Transfection of retroviral packaging cell lines was carried out using a modified version of the $Ca^{2+}$ phosphate co-precipitation protocol. Briefly, 18 hours before transfection, BOSC 23 or BING cells were plated at a density of $2\times10^6$ cells/60 mm tissue culture plate. Just prior to transfection, cell media was replaced with 2 ml of fresh media to which chloroquine had been added to a final concentration of 25 mM. 5 mg of vector DNA was dissolved into 500 ml of 0.2M $CaCl_2$ and 500 ml of 1X Hepes phosphate buffered solution (pH 7.0) was then added. This transfection solution was agitated for 10 seconds and the 1 ml mixture was added directly to the cells. Transfected cells were incubated at 5% $CO_2$ and 37° C. for 8 hours, after which time the media was replaced in order to remove the chloroquine, which can be toxic to cells during extended incubations. Virus prodution and establishement of episomally resident retroviral plasmids.

At 24 hours post-transfection, cells were refed with 3 ml of fresh media and incubated at 32° C. and 5% $CO_2$. For transient titres, virus was harvested at 48 hours post-transfection, placed in 1 ml aliquots (total 3 ml virus for each sample) and frozen at −80° C. After the initial virus collection at 48 hours post-transfection, all cells were trypsinized and placed into 100 mm tissue culture plates containing fresh media and puromycin. Puromycin concentrations of 1 mg/ml and 0.5 mg/ml were used for experiments involving $pBabePuro^{220}$ and LZRS-LacZ, respectively.

Cells were maintained in the selective media until 48 hours prior to any given collection of virus. 48 hours before collecting virus, $2\times10^6$ cells were placed into 60 mm tissue culture plates and overlaid with puromycin-free media. 24 hours later, media was again replaced with 3 ml of fresh puromycin-free media and cells were placed back at 5% $CO_2$ and 32° C. for the production of virus. This procedure was carried out for the production and collection of virus at time points 6, 10, 14, 18 and 30 days post-transfection. Collected virus was placed in 1 ml aliquots and stored at −80° C. to await titering at a later time point.

Infections and titer determinations.

Virus production for the vector pBabePuro$^{220}$ was determined using both the ecotropic BOSC 23 and the amphotropic BING retroviral packaging cell lines. Frozen virus collected from time points 2, 6, 10, 14, 18 and 30 days post-transfection was serially diluted $10^4$, $10^5$ and $10^6$ fold in a total volume of 3 ml. Diluted virus was overlaid onto NIH 3T3 cells that had been plated to a density of $2\times10^5$ cells/60 mm tissue culture plate at 24 hours prior to infection. Polybrene was then added to the virus-containing media to a final concentration of 8 mg/ml. Cells were incubated at 37° C. and 5% $CO_2$ for 24 hours, after which time the media was replaced with fresh media and cells were incubated under identical conditions for an additional 24 hours. At 48 hours post-infection, all cells were trypsinized and plated into 100 mm tissue culture plates containing 15 ml of media that had been supplemented with puromycin to a final concentration of 2.5 mg/ml. After 5 days of puromycin selection the media was carefully replaced with 15 ml of fresh, puromycin containing media (final concentration 2.5 mg/ml) and resistant clones were allowed to grow for an additional 8 days. Colonies were determined by ethanol fixation and methylene blue staining as previously described.

LZRS-LacZ virus production capabilities were determined using the BOSC 23 retroviral packaging cell line. Dilution and infection procedures were identical to the above described procedure. Determination of viral titer was accomplished by fluorosine FACS analysis.

Episome stability analysis.

BOSC 23 cells transfected with pBabePuro$^{220}$ and maintained in puromycin selection are harvested at days 6, 13, 17 and 30 and Hirt extractions performed. Isolated vector DNA is subjected to digestion with DpnI to remove any non-mammalian replicated DNA and subsequently electroporated into E. Coli Stable II cells (Stratagene). After a one hour incubation at 37° C., electroporated bacteria are plated on LB/AMP (100 mg/ml) plates and placed at 37° C. Bacterial colonies are counted 16 hours later. 5 individual colonies selected from each time point are grown overnight in liquid LB/AMP cultures and plasmid DNA isolated by standard miniprep procedures. Isolated DNA are then analyzed for gross rearrangements by digestion with Sal I, BamHI, Nhe I and Sac II.

RESULTS

Construction of hybrid EBV/retroviral vectors.

Three prototype vectors were constructed. The first of these constructs, designated as pBabePuro220 (aka pEBVretPuro) (FIG. 1), was constructed in a series of steps from the retroviral vector pBabePuro and the Epstein-Barr virus based plasmid p220.2. The SV40 early promoter present within pBabePuro contains replication sequences that are capable of mediating high copy number replication in the presence of SV40 large T-antigen. Both the BOSC 23 and the BING retroviral packaging cell lines stably express a temperature sensitive version of the SV40 large T-antigen. In order to avoid potentially confusing results, it was necessary to ensure the absence of these sequences from the first of the prototype vectors. Additionally, the EcoRI-BamHI fragment derived from p220.2 contains termination sequences from the HSV-1 thymidine kinase gene. These sequences prevent opposing transcriptional run-through into the EBV Orip cis elements which, if left unchecked, can suppress Orip mediated replication.

Figure 2:
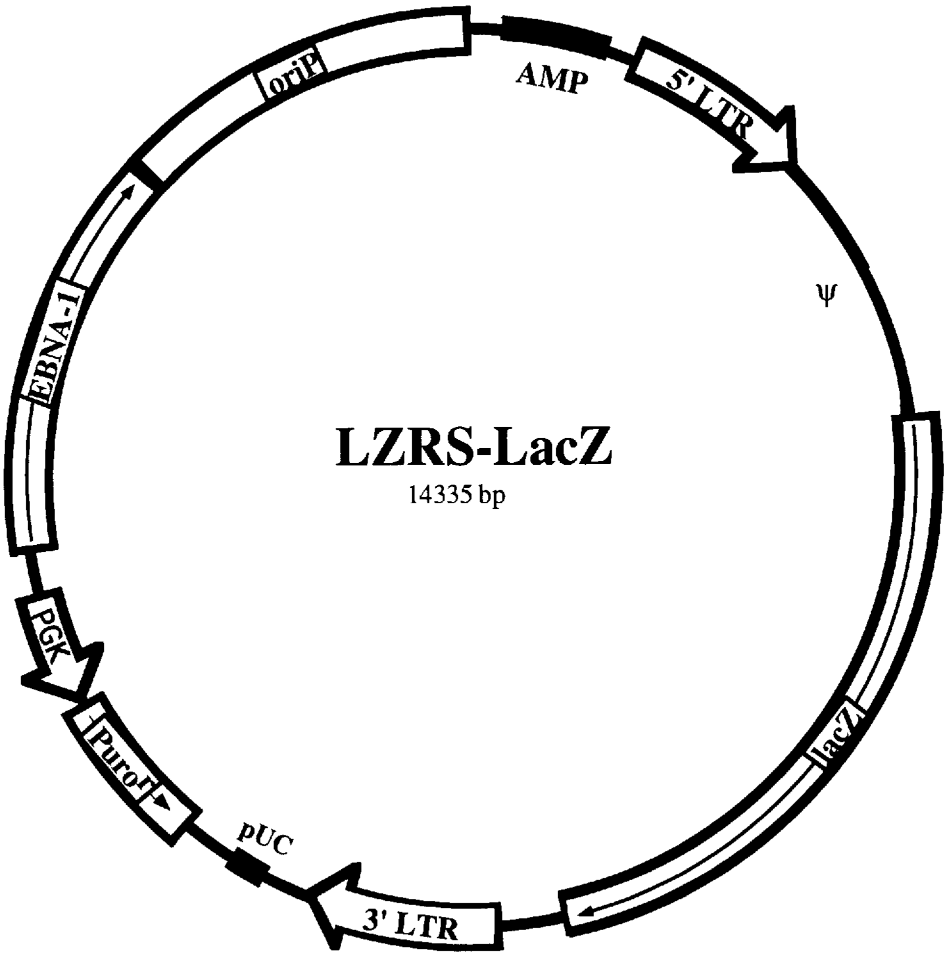
FIG. 2. Design of LZRS-Lac Z vector.
Figure 3:
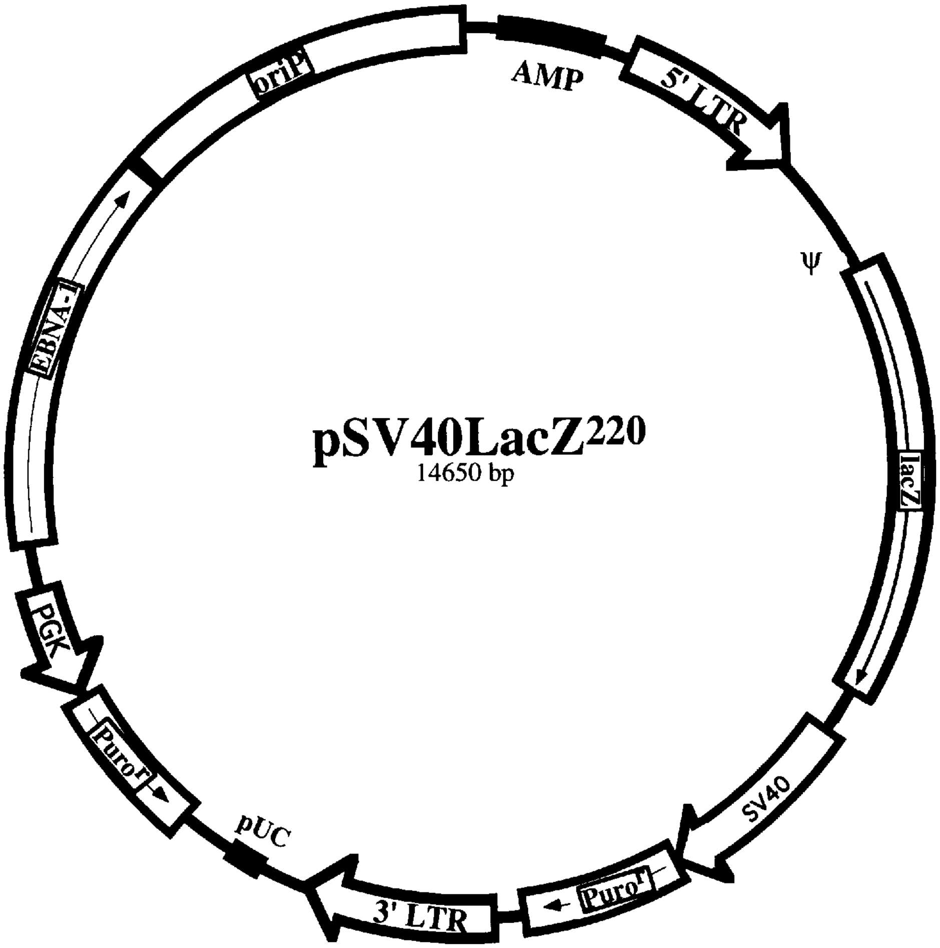
FIG. 3. Design of pSV40LacZ220 vector.

LZRS-LacZ (FIG. 2) differs organizationally from pBabePuro$^{220}$ in that the puromycin resistance gene, now under the control of the Phosphoglycerol kinase-1 promoter, has been moved into non-retroviral portions of the vector. This reorganization continued to allow rapid selection of transduced packaging cells while freeing up potential subcloning space within retroviral portions of the hybrid vectors. In addition, 5' LTR and Y packaging sequences present within this vector were derived from the MFG series of retroviral vectors.

pSV40LacZ$^{220}$ (FIG. 3) was constructed in order to test the utility of SV40 replication sequences as potential tools for transiently boosting vector copy number and therefore the virus production capabilities of these hybrid vectors. The SV40 early promoter present within this vector contains sequences which are capable of functioning as lytic origins of replication in the presence of SV40 large T-antigen.

Long term virus production.

To test the short term and long term ability of these hybrid vectors to produce retrovirus, the pBabePuro$^{220}$ construct was transfected into both the ecotropic BOSC 23 and the amphotropic BING retroviral packaging cell lines. Two days after transfection, virus was collected from the transfected cells (day 2 virus) and frozen. The transfected cells were split into puromycin selection conditions. Thereafter, virus was collected on days 6, 10, 14, 18 and 30. Infection of NIH 3T3 cells with virus from the various time points demonstrated the ability of these hybrid vectors to produce high titers of virus as soon as 48 hours and for as long as 30 days after transfection. (Table 4).

TABLE 4

| TIME POINT | SAMPLE | dilution ($10^4$) | dilution ($10^5$) | dilution ($10^6$) |
|---|---|---|---|---|
| 2 days post-transfection | OZ1 | $3.71 \times 10^6$ | $1.2 \times 10^7$ | |
| | OZ2 | $3.49 \times 10^6$ | $3.8 \times 10^8$ | $1.4 \times 10^7$ |
| | Bosc3 | Monolayer | $2.4 \times 10^7$ | $9.9 \times 10^7$ |
| | Bosc4 | Monolayer | $2.0 \times 10^7$ | $2.0 \times 10^7$ |
| | Bosc5 | Monolayer | $1.3 \times 10^7$ | $3.4 \times 10^7$ |
| | Bosc7 | 0 | | |
| 6 days post-transfection | OZ1 | $1.18 \times 10^6$ | $1.3 \times 10^7$ | $5.8 \times 10^7$ |
| | OZ2 | Monolayer | *$2.4 \times 10^7$ | $1.6 \times 10^8$ |
| | Bosc3 | Monolayer | $3.6 \times 10^7$ | $1.6 \times 10^8$ |
| | Bosc4 | Monolayer | *$2.4 \times 10^7$ | $8.0 \times 10^7$ |
| | Bosc5^ | $5.00 \times 10^5$ | $1.8 \times 10^6$ | $3.2 \times 10^7$ |
| 10 days post-transfection | OZ1 | Monolayer | $1.4 \times 10^7$ | $4.2 \times 10^7$ |
| | OZ2 | Monolayer | ’$1.5 \times 10^7$ | $1.6 \times 10^8$ |
| | Bosc3 | Monolayer | ’$2.1 \times 10^7$ | $6.1 \times 10^8$ |
| | Bosc4 | Monolayer | ’$1.4 \times 10^7$ | $7.8 \times 10^7$ |
| | Bosc5# | no virus collected | | |
| 14 days post-transfection | OZ1 | Monolayer | ’$2.1 \times 10^7$ | $1.0 \times 10^8$ |
| | OZ2 | Monolayer | $1.6 \times 10^7$ | $8.3 \times 10^7$ |
| | Bosc3 | Monolayer | $2.7 \times 10^7$ | $8.7 \times 10^7$ |
| | Bosc4 | Monolayer | $2.5 \times 10^7$ | $4.7 \times 10^7$ |
| 18 days post-transfection | OZ1 | Monolayer | ’$2.2 \times 10^7$ | $1.2 \times 10^8$ |
| | OZ2 | Monolayer | ’$1.3 \times 10^7$ | $8.3 \times 10^7$ |
| | Bosc3 | Monolayer | ’$1.7 \times 10^7$ | $8.7 \times 10^7$ |
| | Bosc4 | Monolayer | ’$1.6 \times 10^7$ | $4.7 \times 10^7$ |
| 30 days post-transfection | OZ1 | ’...$3.22 \times 10^6$ | ’$1.7 \times 10^7$ | $9.1 \times 10^7$ |
| | OZ2 | ’$1.79 \times 10^6$ | ’$8.0 \times 10^6$ | $4.8 \times 10^7$ |
| | Bosc3 | Monolayer | ’$1.0 \times 10^6$ | $4.0 \times 10^6$ |
| | Bosc4 | Monolayer | ’$6.9 \times 10^6$ | $1.9 \times 10^7$ |

OZ1-Bing retroviral packaging cell line transfected with pEBVretroPuro
OZ2-Bing retroviral packaging cell line transfected with pEBVretroPuro
BOSC3 Bosc retroviral packaging cell line transfected with pEBVretroPuro
BOSC4 Bosc retroviral packaging cell line transfected with pEBVretroPuro TABLE 4-continued

| TIME POINT | SAMPLE | dilution ($10^4$) | dilution ($10^5$) | dilution ($10^6$) |
|---|---|---|---|---|

BOSC5 Bosc retroviral packaging cell line transfected with pRetroPuro
BOSC7 Bosc retroviral packaging cell line. No DNA in transfection (negative control
^Cell Number is dropping in this Bosc 5 due to rapid cell death
#99% Bosc 5 cells dead, no virus collected at 10 and 14 days post-transfection.
'Monolayer indicates too many overlapping colonies to get an accurate count.
*May be an underestimation of titer due to overgrowth/overlapping of clonal colonies.

In subsequent experiments, the pBabePuro$^{220}$ LZRS-, LZRS constructs were similarly transfected into the ecotropic BOSC 23 retroviral packaging cell line. Two days after transfection, virus was collected from the transfected cells (day 2 virus) and frozen. The transfected cells were split into puromycin selection conditions. Thereafter, virus was collected on days, 10, and 28. Infection of NIH 3T3 cells with virus from the time points demonstrated the ability of these hybrid vectors to produce high titers of virus as soon as 48 hours and for as long as 28 days after transfection (Table 5).

TABLE 5

| TIME POINT | SAMPLE | dilution 1:50 | dilution 1:100 | dilution 1:1000 |
|---|---|---|---|---|
| 2 days post-transfection | MFG-LacZ | $3.5 \times 10^5$ | $3.8 \times 10^5$ | |
| | pBabeM | $7.7 \times 10^5$ | $8.6 \times 10^5$ | $1.3 \times 10^6$ |
| | LZRS-LacZ | $3.0 \times 10^6$ | $3.5 \times 10^6$ | $2.7 \times 10^6$ |
| 10 days post-transfection | LZRS-LacZ | $3.0 \times 10^6$ | $2.4 \times 10^6$ | $2.5 \times 10^6$ |
| 28 days post-transfection | LZRS-LacZ | $2.0 \times 10^6$ | $2.4 \times 10^6$ | $3.0 \times 10^6$ |

Figure 4:
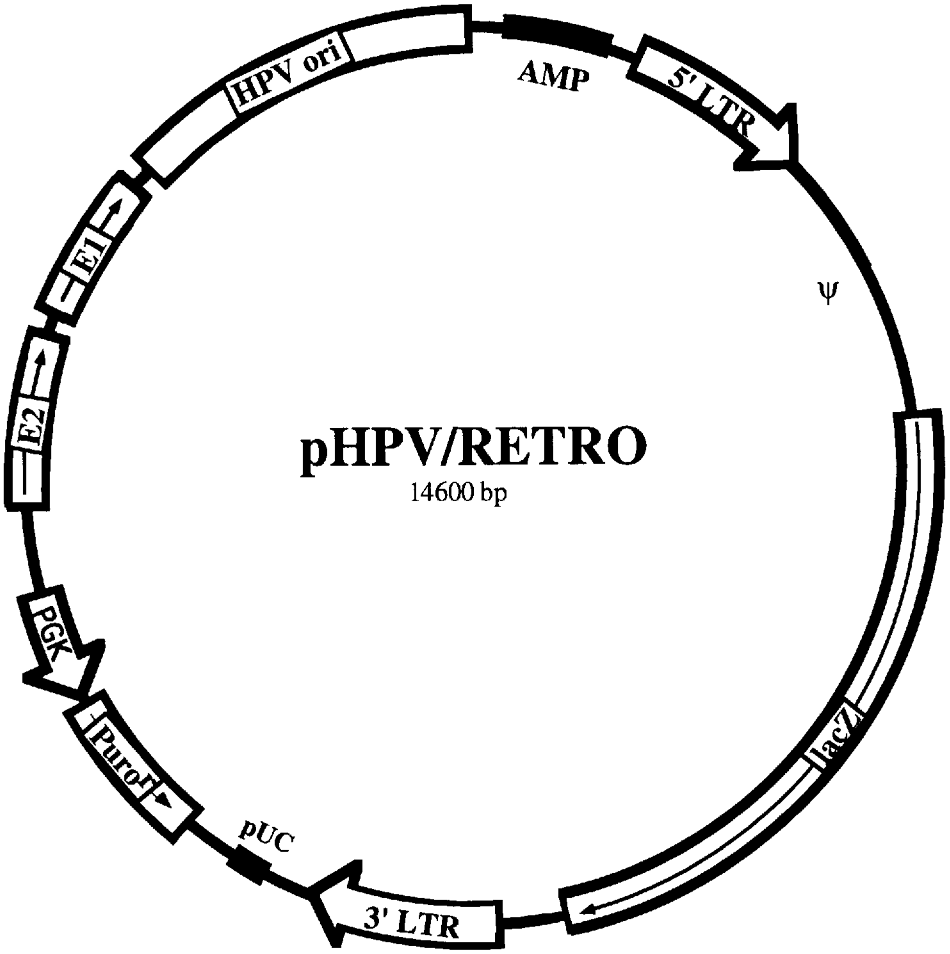
FIG. 4. Design of pHPV/RETRO vector.

The pHPV/RETRO construct (FIG. 4) may be transfected into human packaging cell lines as above or into murine packaging lines such as 3T3. For 3T3 cells, liposome-mediated transfections are preferred; otherwise, infections and titer assays are as described above. Using the NIH 3T3 cell line, titers in exess of $3\times10^7$ are maintained 28 days post-infection (Table 6).

TABLE 6

| TIME POINT | SAMPLE | dilution 1:50 | dilution 1:100 | dilution 1:1000 |
|---|---|---|---|---|
| 2 days post-transfection | MFG-LacZ | $>3.0 \times 10^7$ | $>3.0 \times 10^7$ | $>3.0 \times 10^7$ |
| | pHPV/RETRO | $>3.0 \times 10^7$ | $>3.0 \times 10^7$ | $>3.0 \times 10^7$ |
| 10 dyas post-transfection | pHPV/RETRO | $>3.0 \times 10^7$ | $>3.0 \times 10^7$ | $>3.0 \times 10^7$ |
| 28 days post-transfection | pHPV/RETRO | $>3.0 \times 10^7$ | $>3 \times 10^7$ | $>3.0 \times 10^7$ |

The ability to select transfected cells with puromycin (this drug has been chosen due to its low cost relative to other selectable markers such as G418/neo and Hygromycin/hyg and rapid killing of cells not expressing the pac gene for puromycin resistance) ensured a pure population of producer cells and resulted in increases in viral titers from that obtained after a transient transfection. Rescue experiments with β-galactosidase assays were unable to detect the presence of any rescued LacZ virus, indicting that virus produced from the hybrid vectors at all time points after transfection was free of helper virus.

Since most retroviral vectors do not provide EBNA/EBV ori, we also designed a series of vectors for accepting a variety of retroviral backbones using several different sets of restriction enzymes in the retroviral LTR region. Thse vectors comprise a more efficient retroviral LTR/packaging region, based upon the MFG retroviral backbone of Mulligan et al., a suitable polylinker region and a puromycin selectable marker placed outside the retroviral backbone. In addition, the vector contains only the EBV ori sequences so it may be used in systems in which EBNA is provided from a chromosomally integrated construct. This minimizes the possibility of EBNA sequences non-homologously entering the retroviral backbone during transient transfection and episomal maintenance period, enhancing the systems' value in gene therapy applications. For example, a particular construct contains a puromycin resistance gene expressed from the pgk promoter (to ensure compatibiltiy with T antigen containing 293 cells).

Episomal Stabilty.

Hirt extraction of transfected packaging cells at days 6, 13, 17 and 30 and electroporation into E. coli Stable II (Stratagene) cells demonstrate that these constructs are episomally maintained within packaging cells at an estimated copy number of 10–50 per cell. The restriction analyses of vector DNA isolated from 50 individual bacterial colonies indicate that no gross rearrangements occurrs within these hybrid vectors at any of the time points after transfection.

Amplification of virus titer by SV40 replication functions.

The BOSC 23 and the BING retroviral packaging cell lines express a temperature sensitive version of the SV40 replication protein, large T-antigen. To test the ability of SV40 Ori sequences to amplify vector copy number and increase the virus production from our hybrid vectors, pBabePuroLacZ$^{220}$ is transfected into BOSC 23 cells. 24 hours later, cells are placed at 32° C., the permissive temperature for large T-antigents, or 37° C. After 24 hours of incubation at the designated temperature, all transfected cells are refed with 3 ml fresh media and placed at 37° C. for virus production. 24 hours later, virus is collected and frozen at −80° C. Infection of NIH 3T3 cells demonstrates that the 32° C. amplification step is able to increase vector copy number approximately 100 fold. This amplification results in a 10 fold increase in the total yield of infectious virus, producing titers as high as $5.5\times10^8$ CFU/ml. Various control vectors demonstrate that the increase in viral titers produced by the 32° C. incubation is due to large increases in vector copy number. Hirt analysis indicate no additional propensity of these amplified vectors to produce helper virus or to undergo gross sequence rearrangements after large T-antigen/SV40 Ori mediated amplification.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for making high titre helper-free retrovirus comprising steps:

(a) growing a transfected host cell produced by transfecting a eukaryotic host cell with a recombinant vector, wherein said recombinant vector is stably maintained as an episome in said transfected host cell and transcripts of said vector form, with retroviral gag, pol and env gene products, an infectious retrovirus, said vector comprising:

(i) a retroviral construct comprising an exogenous gene;

(ii) a eukaryotic origin of replication sequence providing a substrate for replicase activity which replicates said vector in said host cell; and, (iii) a copy control sequence providing a substrate for a copy control activity which maintains said vector at a stable copy number in said host cell;

said transfected host cell providing retroviral pol reverse transcriptase and integrase activity, said replicase activity and said copy control activity, as well as said retroviral gag, pol and env gene products which activities and gene products form, with a transcript of said retroviral construct, an infectious retrovirus; and, (b) isolating from said medium helper-free infectious retrovirus comprising said exogenous gene, said retrovirus formed in said transfected host cell.

2. A method according to claim 1, wherein said copy control sequence is a Herpes virus sequence.

3. A method according to claim 1, wherein said copy control sequence comprises at least a portion of the Epstein-Barr virus Ori sequence sufficient to provide a substrate for said copy control activity.

4. A method according to claim 1, wherein said copy control activity is provided by a Herpes virus protein.

5. A method according to claim 1, wherein said copy control activity is provided by Epstein-Barr Virus Nuclear Antigen.

6. A method according to claim 1, wherein said vector encodes said copy control activity and said copy control activity is provided by a Herpes virus protein.

7. A method according to claim 1 wherein said recombinant vector further comprises a eukaryotic selectable marker operably linked to a transcription regulatory element and said medium comprises a selective agent, which agent permits the selective growth of eukaryotic cells expressing said eukaryotic selectable marker.

8. A method according to claim 1 wherein said recombinant vector further comprises a prokaryotic selectable marker operably linked to a transcription regulatory element and a prokaryotic origin of replication sequence providing a substrate for replicase activity capable of replicating said vector in a prokaryotic cell.

9. A method according to claim 1 wherein both said eukaryotic origin of replication and said copy control sequence of said recombinant vector are provided by a single continuous viral ori sequence.

10. A method according to claim 1, wherein said host cell is stably transfected with nucleic acid encoding said retroviral gag and pol genes, said genes operably linked to a transcription regulatory element.

11. A method according to claim 1, wherein said host cell is stably transfected with nucleic acid encoding a viral gene, the transcription product of said viral gene providing both said replicase and said copy control activity.

12. A method according to claim 1, wherein said isolating step comprises isolating at least $10^7$ helper-free infectious retrovirus per milliliter of said medium.

13. A method according to claim 1, wherein said isolating step comprises isolating at least $10^8$ helper-free infectious retrovirus per milliliter of said medium.

14. A method according to claim 1 wherein said recombinant vector further comprises a eukaryotic selectable marker operably linked to a transcription regulatory element, a prokaryotic selectable marker operably linked to a transcription regulatory element, a prokaryotic origin of replication sequence providing a substrate for replicase activity capable of replicating said vector in a prokaryotic cell, a transcription regulatory element operably linked to said exogenous gene; said medium comprises a selective agent permit the selective growth of eukaryotic cells expressing said eukaryotic selectable marker; said copy control sequence comprises at least a portion of the Epstein-Barr virus Ori sequence and said copy control activity is provided by Epstein-Barr Virus Nuclear Antigen; said host cell is stably transfected with nucleic acid comprising gag and pol genes encoding said gag and pol gene products, said gag and pol genes operably linked to a transcription regulatory element; and said isolating step comprises isolating at least $10^7$ helper-free infectious retrovirus per milliliter of said medium.

15. A recombinant vector capable of stable episomal maintenance in a eukaryotic host cell, said vector comprising:

(a) a retroviral construct comprising an exogenous gene;

(b) a eukaryotic origin of replication sequence providing a substrate for a replicase activity which replicates said vector in said host cell; and, (c) a copy control sequence providing a substrate for a copy control activity which maintains said vector at a stable copy number in said host cell.

16. A recombinant vector according to claim 15, wherein said copy control sequence is a Herpes virus sequence.

17. A recombinant vector according to claim 15, wherein said copy control sequence comprises at least a portion of the Epstein-Barr virus Ori sequence sufficient to provide a substrate for said copy control activity.

18. A recombinant vector according to claim 15, wherein said vector encodes said copy control activity and said copy control activity is provided by a Herpes virus protein.

19. A recombinant vector according to claim 15, wherein said vector encodes said copy control activity and said copy control activity is provided by Epstein-Barr Virus Nuclear Antigen.

20. A recombinant vector according to claim 15 further comprising a eukaryotic selectable marker operably linked to a transcription regulatory element.

21. A recombinant vector according to claim 15 further comprising a prokaryotic selectable marker operably linked to a transcription regulatory element and a prokaryotic origin of replication sequence providing a substrate for replicase activity capable of replicating said vector in a prokaryotic cell.

22. A recombinant vector according to claim 15 further comprising a eukaryotic selectable marker operably linked to a transcription regulatory element, a prokaryotic selectable marker operably linked to a transcription regulatory element, a prokaryotic origin of replication sequence providing a substrate for replicase activity which replicates said vector in a prokaryotic cell; said copy control and said eukaryotic origin of replication sequences comprising at least a portion of the Epstein-Barr virus Ori sequence sufficient to provide a substrate for said copy control activity; said vector encodes said copy control activity and said copy control activity is provided by Epstein-Barr Virus Nuclear Antigen.

23. A host cell comprising a recombinant vector according to claim 15, said retroviral pol reverse transcriptase and integrase activity, said replicase activity and said copy control activity, as well as retroviral gag and env gene products which activities and gene products form, with a transcript of said retroviral construct, an infectious retrovirus.

* * * * *

SEQUENCE LISTING (1) GENERAL INFORMATION:

(iii) NUMBER OF SEQUENCES: 9

(2) INFORMATION FOR SEQ ID NO:1:

(i) SEQUENCE CHARACTERISTICS:
(A) LENGTH: 352 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:1:

```
UGGCCAGCAA CUUAUCUGUG UCUGUCCGAU UGUCUAGUGU CUAUGACUGA UUUUAUGCGC    60
CUGCGUCGGU ACUAGUUAGC UAACUAGCUC UGUAUCUGGC GGACCCGUGG UGGAACUGAC   120
GAGUUCGGAA CACCCGGCCG CAACCCUGGG AGACGUCCCA GGGACUUCGG GGGCCGUUUU   180
UGUGGCCCGA CCUGAGUCCA AAAAUCCCGA UCGUUUUGGA CUCUUUGGUG CACCCCCCUU   240
AGAGGAGGGA UAUGUGGUUC UGGUAGGAGA CGAGAACCUA AAACAGUUCC CGCCUCCGUC   300
UGAAUUUUUG CUUUCGGUUU GGGACCGAAG CCGCGCCGCG CGUCUUGUCU GC           352
```

(2) INFORMATION FOR SEQ ID NO:2:

(i) SEQUENCE CHARACTERISTICS:
(A) LENGTH: 46 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:2:

```
CGCCAAAAAT TTTGACTAGC GGAGGCTAGA AGGAGAGAGA TGGGTG                   46
```

(2) INFORMATION FOR SEQ ID NO:3:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:3:

```
UGGCGCCCGA ACAGGGAC                                                  18
```

(2) INFORMATION FOR SEQ ID NO:4:

(i) SEQUENCE CHARACTERISTICS:
(A) LENGTH: 18 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

```
UGGGGGCUCG UCCGGGAU                                                  18
```

(2) INFORMATION FOR SEQ ID NO:5:

-continued ( i ) SEQUENCE CHARACTERISTICS:
( A ) LENGTH: 18 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:5:

UGGUGACCCC GACGUGAU 18

( 2 ) INFORMATION FOR SEQ ID NO:6:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:6:

AGTGAATTAG CCCTTCCAGT 20

( 2 ) INFORMATION FOR SEQ ID NO:7:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:7:

TGTGGAAAAT CTCTAGCAGT 20

( 2 ) INFORMATION FOR SEQ ID NO:8:

( i ) SEQUENCE CHARACTERISTICS:
( A ) LENGTH: 11 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:8:

AATGAAAGAC C 11

( 2 ) INFORMATION FOR SEQ ID NO:9:

( i ) SEQUENCE CHARACTERISTICS:
( A ) LENGTH: 12 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:9:

GGGTCTTTCA TT 12